United States Patent
Svangård et al.

(10) Patent No.: US 11,094,188 B2
(45) Date of Patent: Aug. 17, 2021

(54) SYSTEM AND METHOD FOR MONITORING AN INDIVIDUAL

(71) Applicant: Pink Nectarine Health AB, Stockholm (SE)

(72) Inventors: Nils Svangård, Stockholm (SE); Tor Carlsson, Stockholm (SE)

(73) Assignee: PINK NECTARINE HEALTH AB, Stockholm (SE)

( * ) Notice: Subject to any disclaimer, the term of this patent is extended or adjusted under 35 U.S.C. 154(b) by 0 days.

(21) Appl. No.: 15/930,890

(22) Filed: May 13, 2020

(65) Prior Publication Data
US 2021/0097848 A1 Apr. 1, 2021

(30) Foreign Application Priority Data
Sep. 30, 2019 (SE) .................................... 1951107-0

(51) Int. Cl.
G08B 29/18 (2006.01)
G08B 21/04 (2006.01)

(52) U.S. Cl.
CPC ......... *G08B 29/185* (2013.01); *G08B 21/043* (2013.01); *G08B 21/0446* (2013.01); *G08B 21/0453* (2013.01)

(58) Field of Classification Search
CPC .............. G08B 21/043; G08B 21/0446; G08B 21/0453
(Continued)

(56) References Cited

U.S. PATENT DOCUMENTS 8,810,388 B2 * 8/2014 Jacobs ................ G08B 21/043
340/521
10,335,059 B2 7/2019 Annegarn et al.
(Continued)

FOREIGN PATENT DOCUMENTS

WO 2011/004322 A1 1/2011
WO WO-2018/168604 A1 9/2018
WO 2019/075381 A2 4/2019

OTHER PUBLICATIONS

Kostopoulos, Panagiotis et al., "F2D: A fall detection system tested with real data from daily life of elderly people," 2015 17th International Conference on E-health Networking, Application & Services (HealthCom), Oct. 2015, pp. 397-403.
(Continued)

*Primary Examiner* — John A Tweel, Jr.
(74) *Attorney, Agent, or Firm* — Faegre Drinker Biddle & Reath LLP

(57) ABSTRACT

In accordance with one or more embodiments herein, a system for monitoring an individual within predetermined facilities 500 in order to determine whether there is a need for setting an alert is provided. The system 100 comprises: a personal module 200 to be worn by the monitored individual, the personal module 200 comprising at least one motion sensor 220; at least one node module 300, with which the personal module 200 is arranged to communicate; a storage means 320; and at least one processing device 210, 310, 160. The at least one processing device 210, 310, 160 may be arranged to: receive sensor data from the at least one motion sensor 220 in the personal module 200; determine whether the received sensor data indicates a specific alert state among a plurality of predetermined alert states, the alert states comprising at least a FALL alert state, to be used if a probable fall has been detected for the monitored individual, and an OUT OF BED alert state, to be used if it
(Continued)

has been detected that the monitored individual is probably getting out of bed; determine the distance between the personal module 200 and the at least one node module 300; determine the location of the personal module 200 within the facilities 500 based at least on the determined distance together with information retrieved from the storage means 320 regarding the layout of the facilities 500 within which the monitoring of the individual takes place; and set an alert based at least on whether the received sensor data indicates an alert state and whether the determined location fulfils a predetermined location condition, indicating whether the individual is located in a certain room, such as e.g. the bedroom 530.

20 Claims, 4 Drawing Sheets

(58) Field of Classification Search
USPC .......................................................... 340/521
See application file for complete search history.

(56) References Cited

U.S. PATENT DOCUMENTS

| | | |
|---|---|---|
| 2012/0190949 A1 | 7/2012 | McCombie et al. |
| 2013/0060167 A1 | 3/2013 | Dracup et al. |
| 2013/0141233 A1 | 6/2013 | Jacobs et al. |
| 2019/0231280 A1 | 8/2019 | Tudor |
| 2019/0239775 A1 | 8/2019 | Movva et al. |

OTHER PUBLICATIONS

Shastry, Mahesh C. et al., "Context-Aware Fall Detection Using Inertial Sensors and Time-of-Flight Transceivers," 38th Annual International Conference of the IEEE Engineering in Medicine and Biology Society (EMBC), Aug. 2016, pp. 570-573.
Notice with Swedish Search Report dated Mar. 13, 2020 for corresponding Swedish Application No. 1951107-0.
Written Opinion and International Search Report from International patent application No. PCT/EP2020/077247, dated Jan. 22, 2021.

* cited by examiner

SYSTEM AND METHOD FOR MONITORING AN INDIVIDUAL

TECHNICAL FIELD

The present disclosure relates generally to systems and methods for monitoring an individual within predetermined facilities in order to determine whether there is a need for setting an alert.

BACKGROUND

Elderly, sick or injured people may be prone to falling accidents. Since they may not have the strength or mobility to stand up after a fall has occurred, they may need help in such situations. This could be the case even if the fall itself has not caused any injury. It may therefore be desirable to monitor such an individual so that help can be dispatched when a fall has occurred. Monitoring systems for monitoring such individuals often comprise a personal module (e.g. a wristband) comprising sensors such as e.g. an altimeter and/or an accelerator, the signals of which are analyzed in order to determine a fall.

U.S. Pat. No. 10,335,059 describes such a system where the sensitivity of the fall detection algorithm is increased if the individual has been determined to be at higher risk, such as e.g. if the individual has been determined to presently be walking.

US 2019/0231280 describes such a system where the fall detection is also based on whether there is a period of motion stillness following the fall.

PROBLEMS WITH THE PRIOR ART

It is very difficult to design a system that detects all situations where help is needed after a fall without generating too many false alarms. U.S. Pat. No. 10,335,059 and US 2019/0231280 provide different solutions for addressing this problem, but even with these solutions there will be a high number of false alarms if no falls are to be missed.

There is thus a need for an improved system and method for monitoring an individual.

SUMMARY

The above described problem is addressed by the claimed system for monitoring an individual within predetermined facilities in order to determine whether there is a need for setting an alert. The system may comprise: a personal module to be worn by the monitored individual, the personal module comprising at least one motion sensor; at least one node module, with which the personal module is arranged to communicate; a storage means; and at least one processing device. The at least one processing device may be arranged to: receive sensor data from the at least one motion sensor in the personal module; determine whether the received sensor data indicates a specific alert state among a plurality of predetermined alert states, the alert states comprising at least a FALL alert state, to be used if a probable fall has been detected for the monitored individual, and an OUT OF BED alert state, to be used if it has been detected that the monitored individual is probably getting out of bed; determine the distance between the personal module and the at least one node module; determine the location of the personal module within the facilities based at least on the determined distance together with information retrieved from the storage means regarding the layout of the facilities within which the monitoring of the individual takes place; and set an alert based at least on whether the received sensor data indicates an alert state and whether the determined location fulfils a predetermined location condition, indicating whether the individual is located in a certain room, such as e.g. the bedroom.

The above described problem is further addressed by the claimed method for monitoring an individual within predetermined facilities in order to determine whether there is a need for setting an alert. The method may comprise: receiving sensor data from at least one motion sensor arranged in a personal module; determining whether the received sensor data indicates a specific alert state among a plurality of predetermined alert states, the alert states comprising at least a FALL alert state, to be used if a probable fall has been detected for the monitored individual, and an OUT OF BED alert state, to be used if it has been detected that the monitored individual is probably getting out of bed; determining the distance between the personal module and at least one node module; determining the location of the personal module within the facilities based at least on the determined distance together with information retrieved from a storage means regarding the layout of the facilities within which the monitoring of the individual takes place; and setting an alert based at least on whether the received sensor data indicates an alert state and whether the determined location fulfils a predetermined location condition, indicating whether the individual is located in a certain room, such as e.g. the bedroom.

The combination of motion information with location information improves the determination of the need for setting an alert, since e.g. an OUT OF BED alert should only be issued if the monitored individual is in the bedroom.

In embodiments, the determination of whether the received sensor data indicates an alert state among a plurality of predetermined alert states is done by a trained machine learning algorithm. Machine learning is an efficient way of evaluating complex signals in situations where large amounts of data is collected.

In embodiments, the location of the personal module is determined based also on an indication of the movement of the individual in relation to a previously determined location, based on sensor data from the at least one motion sensor. If the individual is determined to be in a certain location, and the movement required for moving to this location from a previously determined location is more than the movement that has been detected by the at least one movement sensor, it is likely that the determined location is incorrect.

In embodiments, an activity state for the monitored individual is continuously determined and updated. The activity state may e.g. categorize the current activity of the individual. Activity states may e.g. be LYING IN BED, LYING ON COUCH, LYING ON FLOOR, SITTING, STANDING, WALKING, RUNNING, RIDING A WHEELCHAIR, WALKING UP/DOWN STAIRS, IN THE BATHROOM. There may also be a specific activity state for when the individual is not wearing the personal module, since no other activity state can then be set.

In embodiments, the alert is set based also on at least one previously determined activity state, e.g. so that the setting of an OUT OF BED alert state also depends on whether the previous activity state was a LYING IN BED activity state, or so that the setting of a FALL alert state also depends on that the previous activity state was not any type of LYING activity state. It is also possible to combine the received sensor data with the activity state without including any determination of a predetermined location condition.

In embodiments, the alert is set based also on the time period for which the individual has had a specific activity state, such as e.g. for how long the individual has been in the activity state STANDING.

In embodiments, the determination of the activity state is done by a trained machine learning algorithm. Machine learning is an efficient way of evaluating complex signals in situations where large amounts of data is collected.

In embodiments, an alarm signal is sent if a predetermined alert is set. This may summon help for the monitored individual in case of e.g. a fall.

In embodiments, the at least one motion sensor is an accelerometer. However, other types of motion sensor may also be used.

In embodiments, the personal module is a wristworn device, such as e.g. a wristband. The personal module may however be any type of device that may be worn by an individual, such as e.g. a necklace or a clip.

In embodiments, the personal module further comprises a personal module communication interface, and the at least one node module further comprises a node module communication interface, which are arranged to communicate with each other.

In embodiments, weighing factors are used in order to combine the different inputs to determine whether an alert should be set. Such weighing factors may be determined by a machine learning system, since this is an efficient way of evaluating complex signals in situations where large amounts of data is collected. For example, the probability for whether an alert should be set may be determined in different ways, that are then combined into a resulting probability, that is compared with a probability threshold.

The at least one processing device may be a personal module processing device, a node module processing device, or another processing device, such as e.g. a remote processing device, which may e.g. be comprised in a web server. The at least one processing device may also be a combination of any number of processing devices, so that some of the processing takes place in one processing device and some of the processing takes place in one or more other processing devices. It is thus not necessary for all of the processing to take place in the same processing device.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Elderly, sick or injured people often carry alarms so that they can summon help if a fall has occurred, or if they need help for some other reason. Systems for monitoring such individuals and automatically issuing alarms in case of e.g. a detected fall have been used for some time. Monitoring systems for monitoring such individuals often comprise a personal module (e.g. a wristband) comprising sensors, the signals of which are analyzed in order to determine whether help is needed, e.g. due to a fall.

It is very difficult to design an algorithm that detects all situations where help is needed without generating too many false alarms. Machine learning is sometimes used for analyzing the signals from the sensors in order to better detect the situations where help is needed. However, since it may be very difficult to detect any general difference between a signal pattern indicating that no help is needed and a signal pattern indicating that an alarm should be issued in order to summon help, even with the use of machine learning there will be many false alarms.

The present disclosure therefore proposes to improve the determination of a need for an alert by combining the analyzed signal with information regarding the location of the monitored individual within the facilities in which the individual is monitored. Embodiments of the disclosed solution are presented in more detail in connection with the figures.

Figure 1:
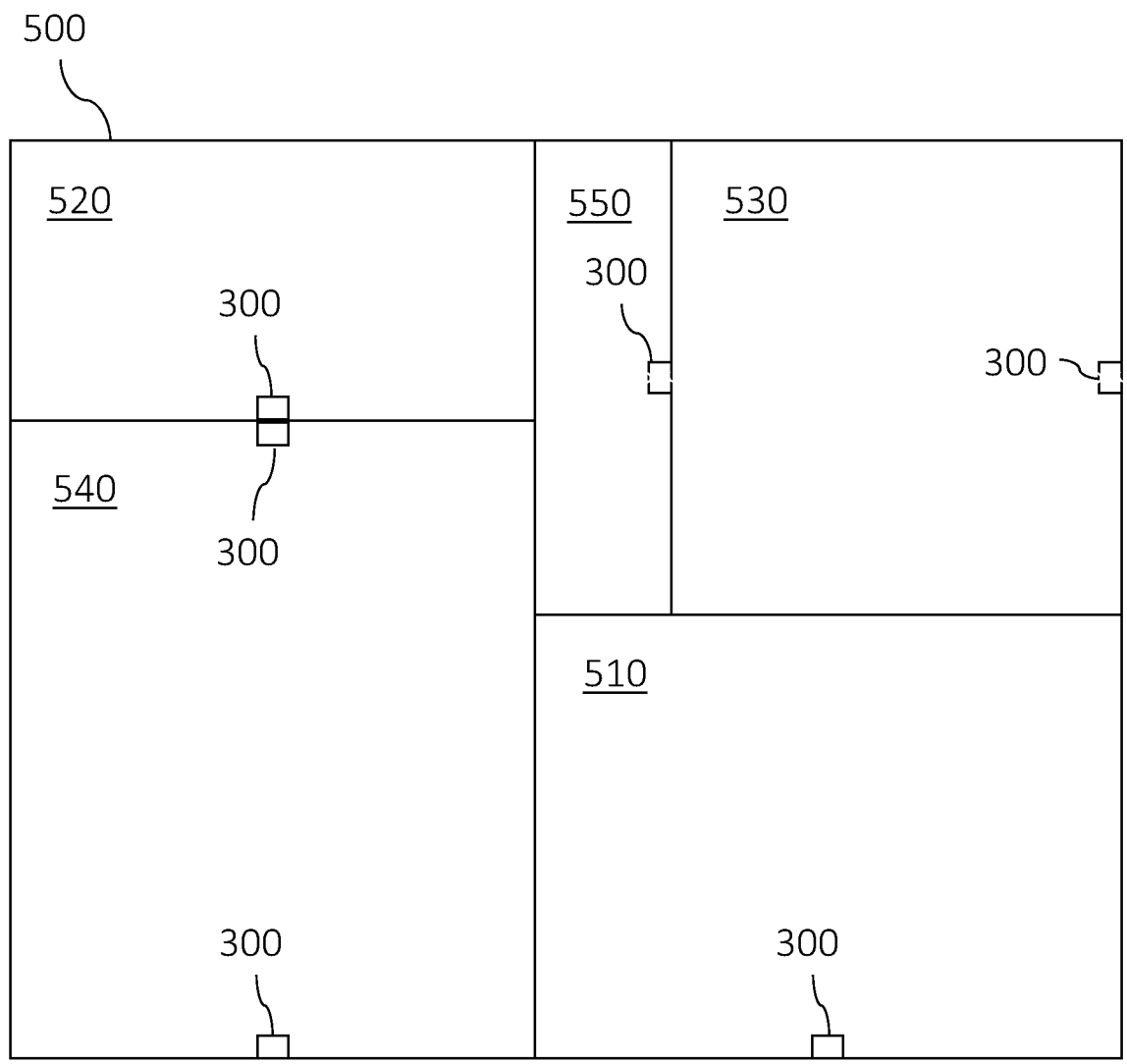
FIG. 1 schematically shows an example of facilities where a monitoring system comprising a number of node modules has been installed, in accordance with one or more embodiments described herein.

FIG. 1 schematically shows an example of facilities 500 where a monitoring system 100 comprising a number of node modules 300 has been installed, in accordance with one or more embodiments described herein. Such facilities 500 may e.g. be an apartment where a monitored individual is residing. Such an apartment 500 may e.g. comprise a kitchen 510, a bathroom 520, a bedroom 530, a sitting room 540, and a hallway 550. The monitoring system 100 may in this case be used by relatives, home care companies or the like.

The facilities 500 may also be other types of quarters where a monitored individual may be residing, such as e.g. a nursing home, where there may be a private space for the monitored individual, including e.g. a bedroom 530, as well as public spaces that are shared by a plurality of monitored individuals.

Figure 2:
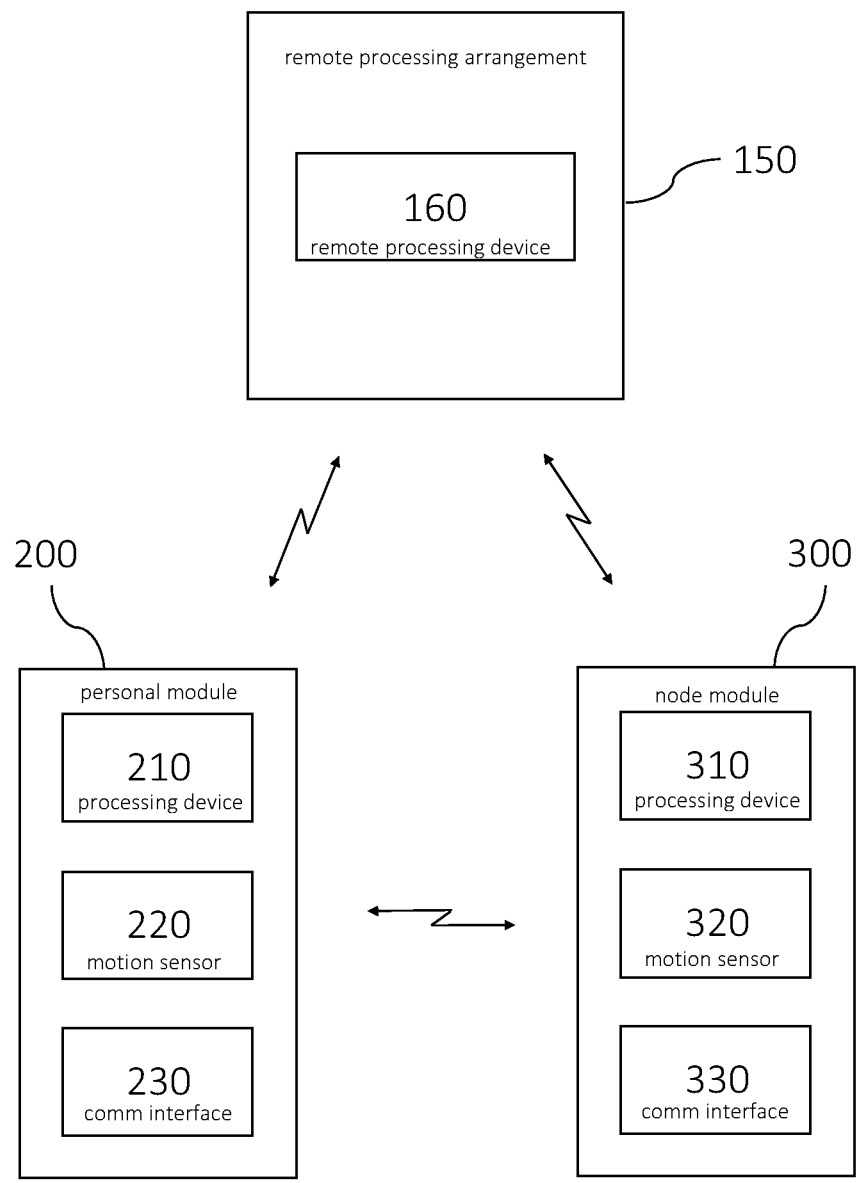
FIG. 2 is a schematic illustration of a system for monitoring an individual within predetermined facilities in order to determine whether there is a need for setting an alert, in accordance with one or more embodiments described herein.

FIG. 2 is a schematic illustration of a system 100 for monitoring an individual within predetermined facilities 500 in order to determine whether there is a need for setting an alert, in accordance with one or more embodiments described herein. The illustrated system 100 comprises a personal module 200, a node module 300, and a remote processing arrangement 150. The illustrated personal module 200 comprises a personal module processing device 210, a motion sensor 220, and a personal module communication interface 230. The illustrated node module comprises a node module processing device 310, a storage means 320, and a node module communication interface 330. The illustrated remote processing arrangement 150 comprises a remote processing device 160, which may e.g. be comprised in a web server. However, the system 100 does not necessarily comprise a remote processing arrangement 150.

Information regarding the layout of the facilities 500, such as the plan of the different rooms and the location of the node modules 300, is preferably stored in the storage means 320. The storage means 320 does not have to be comprised in the node module—it can be comprised in another part of the system, or be a separate module.

At least one processing device 210, 310, 160 of the system 100 may be arranged to: receive sensor data from the at least one motion sensor 220 in the personal module 200; determine whether the received sensor data indicates a specific alert state among a plurality of predetermined alert states, the alert states comprising at least a FALL alert state, to be used if a probable fall has been detected for the monitored individual, and an OUT OF BED alert state, to be used if it has been detected that the monitored individual is probably getting out of bed; determine the distance between the personal module 200 and the at least one node module 300; determine the location of the personal module 200 within the facilities 500 based at least on the determined distance together with information retrieved from the storage means 320 regarding the layout of the facilities 500 within which the monitoring of the individual takes place; and set an alert based at least on whether the received sensor data indicates an alert state and whether the determined location fulfils a predetermined location condition, indicating whether the individual is located in a certain room, such as e.g. the bedroom 530.

The at least one processing device 210, 310, 160 may be the personal module processing device 210, the node module processing device 310, or another processing device, such as a remote processing device 160.

The at least one processing device may also be a combination of any number of processing devices, so that some of the processing takes place in one processing device and some of the processing takes place in one or more other processing devices. It is thus not necessary for all of the processing to take place in the same processing device.

The combination of motion information with location information improves the determination of the need for setting an alert, since e.g. an OUT OF BED alert should only be issued if the monitored individual is in the bedroom 530.

The distance between the personal module 200 and the at least one node module 300 may e.g. be determined based on the received signal strength indication (RSSI), since the received signal strength will be lower if the distance increases. If the RSSI for more than one node module is determined, the location may be more exactly determined based on e.g. triangulation. Machine learning may be used for this determination.

The personal module 200 may also comprise other sensors, such as e.g. a pressure sensor. It is known to use a pressure sensor in a personal module to detect a fall based on a change in pressure. However, a pressure sensor may also be involved in the determination of the location of the individual. If the facilities 500 comprise several floors, and the node modules 300 are arranged in the ceilings or high up on the walls, the RSSI may give erroneous results due to the signals travelling between the floors. In this situation, a pressure sensor may be used to determine the floor on which the individual is located.

In order to improve the determination of the need for setting an alert even further, the determination of the location may be improved by involving also signals from the movement sensor 220. The movement sensor 220 may e.g. be used as a pedometer, so that the signals from the movement sensor 220 indicates how many steps the individual has taken. If the individual is determined to be in a certain location (such as e.g. the bathroom 520), and the amount of steps required for moving to this location from a previously determined location (such as e.g. the bedroom 530) is more than the amount of steps that have been detected by the movement sensor 220, it is likely that the determined location is incorrect. The at least one processing device 210, 310, 160 may thus be arranged to determine the location of the personal module 200 based also on an indication of the movement of the individual in relation to a previously determined location, based on sensor data from the at least one motion sensor 220.

The processing of the sensor data from the at least one motion sensor 220 may be done by a trained machine learning algorithm. When many individuals are monitored using many personal modules 200, large amounts of sensor data is collected from the motion sensors 220 in these personal modules 200. Very efficient evaluation of this sensor data may be done using machine learning, in order to determine a suitable machine learning algorithm.

In order to simplify the determination of the need for alerts, an activity state for the monitored individual may be continuously determined and updated. The activity state may e.g. categorize the current activity of the individual. Activity states may e.g. be LYING IN BED, LYING ON COUCH, LYING ON FLOOR, SITTING, STANDING, WALKING, RUNNING, RIDING A WHEELCHAIR, WALKING UP/DOWN STAIRS, IN THE BATHROOM. There may also be a specific activity state for when the individual is not wearing the personal module, since no other activity state can then be set. There may be a specific sensor, such as e.g. a contact sensor, a temperature sensor or a heart rate sensor, for determining whether the individual is wearing the personal module. Such a sensor may of course also be used for other purposes.

The updating of the activity state for the monitored individual may be incremental, so that only differences in relation to the previously determined activity state need to be determined.

The determination of the activity state may e.g. be done by a trained machine learning algorithm. Machine learning is an efficient way of evaluating complex signals in situations where large amounts of data is collected.

If activity states are set for the monitored individual, the alert may be set based also on at least one previously determined activity state, e.g. so that the setting of an OUT OF BED alert state also depends on whether the previous activity state was a LYING IN BED activity state, or so that the setting of a FALL alert state also depends on that the previous activity state was not any type of LYING activity state. The alert may also be based on the time period for which the individual has had a specific activity state, such as e.g. for how long the individual has been in the activity state STANDING.

It is also possible to combine the received sensor data with the activity state without including any determination of a predetermined location condition.

The information about the activity state may also be combined with information about the location, so that the alert is set also based on where an individual has a certain activity state. For example, if the motion sensor indicates that the individual is lying down, the location may indicate whether the activity is LYING IN BED, LYING ON COUCH, or LYING ON FLOOR.

The at least one processing device 210, 310, 160 may further be arranged to send an alarm signal if a predetermined alert is set. There may be different types of alarms, with different priorities. Examples of alarms needing immediate attention are e.g. FALL, and may also be e.g. OUT OF BED. Other alarms, with lower priority, may e.g. be CHANGE OF BEHAVIOUR, if e.g. the movement pattern of the monitored individual changes, which may be an indication of illness. A larger number of visits to the bathroom may e.g. indicate a urinary infection.

There may also be more technical alerts and alarms, such as e.g. PERSONAL MODULE TAKEN OFF, and PERSONAL MODULE OFFLINE.

Figure 3:
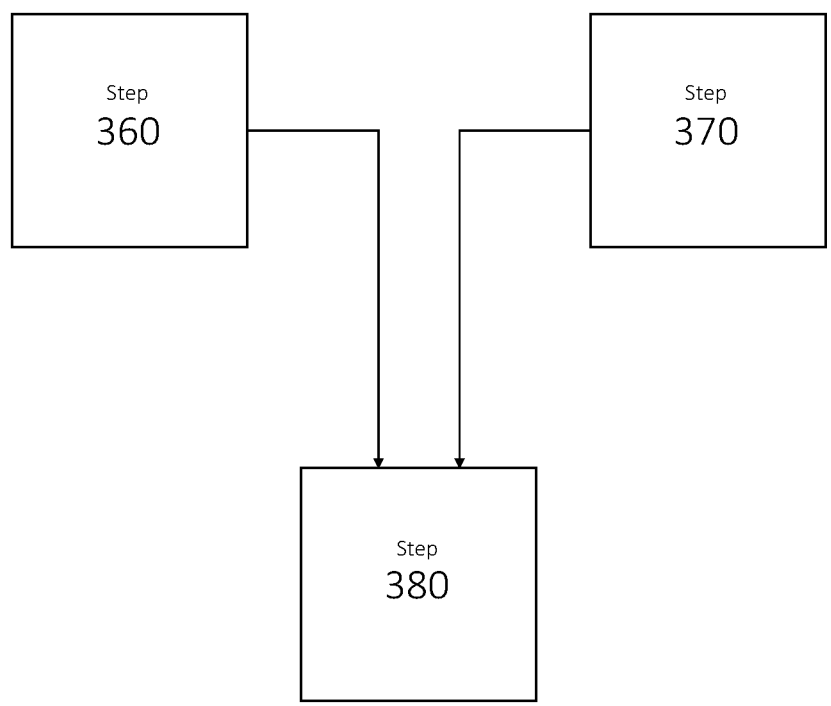
FIG. 3 is an example flow diagram of a method for monitoring an individual within predetermined facilities in order to determine whether there is a need for setting an alert, in accordance with one or more embodiments described herein.

FIG. 3 is an example flow diagram of a method for monitoring an individual within predetermined facilities in order to determine whether there is a need for setting an alert, in accordance with one or more embodiments described herein. The flow 350 may e.g. be as follows:

Step 360: Determine whether the sensor data from the at least one motion sensor 220 indicates a specific alert state.

Step 370: Determine the location of the personal module 200 within the facilities based on the distance between the personal module 200 and at least one node module 300.

Step 380: Combine these inputs into a resulting determination of whether an alert should be set.

The setting of the alert based on a combination of conditions may be done in different ways. Some of the conditions may be conditions that are set absolutely, so that if a certain condition is not fulfilled, the alert will not be set. In other situations, a weighing of different factors is done.

When the alert is set based on whether the received sensor data indicates an alert state and whether the determined location fulfils a predetermined location condition, the predetermined location condition may be an absolute condition, such that if the determined location does not fulfil the predetermined location condition, the alert is not set. However, there may instead be weighing factors, so that if the received sensor data strongly indicates an alert state, and/or the determined location does not strongly indicate a specific location (that does not fulfil the predetermined location condition), the alert will still be set.

If weighing factors are used, these weighing factors may be determined by a machine learning system, since this is an efficient way of evaluating complex signals in situations where large amounts of data is collected.

One way of making such a determination is to determine a probability that an alert should be set based on the received sensor data, and a probability that the determined location fulfils the predetermined location condition, and then combine these probabilities using weighing factors, which may e.g. be determined by a machine learning system.

The same applies to other combinations, such as e.g. the determination of the location by involving also signals from the movement sensor 220, and/or the setting of alerts based also on activity states. These determinations may also be done by determining probabilities and using weighing factors to combine them, which may e.g. be determined by a machine learning system.

Figure 4:
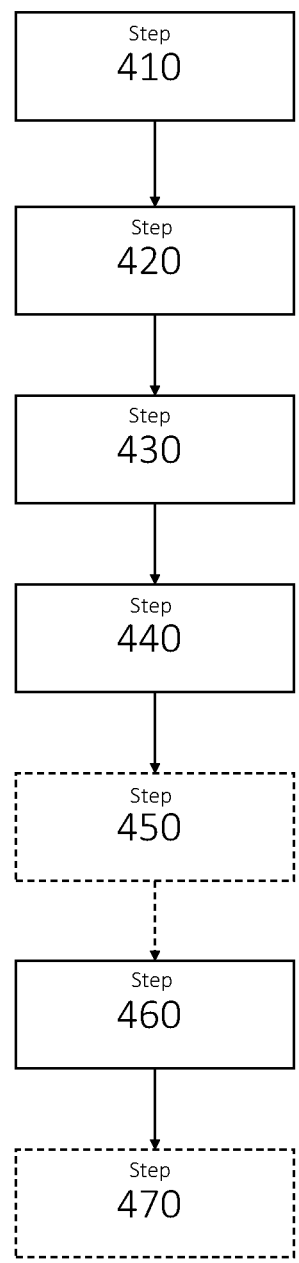
FIG. 4 schematically illustrates a method for monitoring an individual within predetermined facilities in order to determine whether there is a need for setting an alert, in accordance with one or more embodiments described herein.

FIG. 4 schematically illustrates a method 400 for monitoring an individual within predetermined facilities 500 in order to determine whether there is a need for setting an alert, in accordance with one or more embodiments described herein. The method 400 may include the following steps (not necessarily in this order):

Step 410: receiving sensor data from at least one motion sensor 220 arranged in a personal module 200.

Step 420: determining whether the received sensor data indicates a specific alert state among a plurality of predetermined alert states, the alert states comprising at least a FALL alert state, to be used if a probable fall has been detected for the monitored individual, and an OUT OF BED alert state, to be used if it has been detected that the monitored individual is probably getting out of bed.

Step 430: determining the distance between the personal module 200 and at least one node module 300.

Step 440: determining the location of the personal module 200 within the facilities 500 based at least on the determined distance together with information retrieved from a storage means 320 regarding the layout of the facilities 500 within which the monitoring of the individual takes place.

Step 460: setting an alert based at least on whether the received sensor data indicates an alert state and whether the determined location fulfils a predetermined location condition, indicating whether the individual is located in a certain room, such as e.g. the bedroom 530.

The combination of motion information with location information improves the determination of the need for setting an alert, since e.g. an OUT OF BED alert should only be issued if the monitored individual is in the bedroom.

The determining 420 of whether the received sensor data indicates a specific alert state among a plurality of predetermined alert states may e.g. be done by a trained machine learning algorithm, since machine learning is an efficient way of evaluating complex signals in situations where large amounts of data is collected.

The method may involve determining the distance between the personal module 200 and the at least one node module 300 based on the received signal strength indication (RSSI), since the received signal strength will be lower if the distance increases. If the RRSI for more than one node module is determined, the location may be more exactly determined based on e.g. triangulation.

In embodiments, the determining 440 of the location of the personal module 200 is based also on an indication of the movement of the individual in relation to a previously determined location, based on sensor data from the at least one motion sensor 220. If the individual is determined to be in a certain location, and the movement required for moving to this location from a previously determined location is more than the movement that has been detected by the at least one movement sensor, it is likely that the determined location is incorrect.

In embodiments, the at least one motion sensor 220 is an accelerometer. However, other types of motion sensor may also be used.

In embodiments, the personal module 200 is a wristworn device, such as e.g. a wristband. The personal module 200 may however be any type of device that may be worn by an individual, such as e.g. a necklace or a clip.

In embodiments, communication between the personal module 200 and the at least one node module 300 takes place using a personal module communication interface 230 and a node module communication interface 330.

The method 400 may include:

Step 450: continuously determining and updating an activity state for the monitored individual.

The activity state may e.g. categorize the current activity of the individual. Activity states may e.g. be LYING IN BED, LYING ON COUCH, LYING ON FLOOR, SITTING, STANDING, WALKING, RUNNING, RIDING A WHEELCHAIR, WALKING UP/DOWN STAIRS, IN THE BATH- ROOM. There may also be a specific activity state for when the individual is not wearing the personal module, since no other activity state can then be set. There may be a specific sensor, such as e.g. a contact sensor, a temperature sensor or a heart rate sensor, for determining whether the individual is wearing the personal module. Such a sensor may of course also be used for other purposes.

The determining 450 of the activity state may e.g. be done by a trained machine learning algorithm, since machine learning is an efficient way of evaluating complex signals in situations where large amounts of data is collected.

In embodiments, the setting 460 of the alert is based also on at least one previously determined activity state, e.g. so that the setting of an OUT OF BED alert state also depends on whether the previous activity state was a LYING IN BED alert state, or so that the setting of a FALL alert state also depends on that the previous activity state was not any type of LYING activity state.

In embodiments, the setting 460 of the alert is based also on the time period for which the individual has had a specific activity state, such as e.g. for how long the individual has been in the activity state STANDING.

The method 400 may include:

Step 470: sending an alarm signal if a predetermined alert is set.

This may summon help for the monitored individual in case of e.g. a fall.

In embodiments, the method uses weighing factors in order to combine the different inputs to determine whether an alert should be set. Such weighing factors may be determined by a machine learning system, since this is an efficient way of evaluating complex signals in situations where large amounts of data is collected.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

The invention claimed is:

1. A system for monitoring an individual within predetermined facilities in order to determine whether there is a need for setting an alert, the system comprising:
a personal module to be worn by the monitored individual, the personal module comprising at least one motion sensor;
at least one node module, with which the personal module is arranged to communicate;
a storage means; and
at least one processing device, arranged to:
receive sensor data from the at least one motion sensor in the personal module;
determine whether the received sensor data indicates a specific alert state among a plurality of predetermined alert states, the alert states comprising at least a FALL alert state, to be used if a probable fall has been detected for the monitored individual, and an OUT OF BED alert state, to be used if it has been detected that the monitored individual is probably getting out of bed;
determine the distance between the personal module and the at least one node module;
determine the location of the personal module within the facilities based at least on the determined distance together with information retrieved from the storage means regarding the layout of the facilities within which the monitoring of the individual takes place;
determine and update an activity state for the monitored individual; and
set an alert based at least on: whether the received sensor data indicates an alert state; whether the determined location fulfils a predetermined location condition, indicating whether the individual is located in a certain room; and whether at least one previously determined activity state for the monitored individual fulfils a predetermined state condition.

2. The system according to claim 1, wherein the determination of whether the received sensor data indicates an alert state among a plurality of predetermined alert states is done by a trained machine learning algorithm.

3. The system according to claim 1, wherein the at least one processing device is arranged to determine the location of the personal module based also on an indication of the movement of the individual in relation to a previously determined location, based on sensor data from the at least one motion sensor.

4. The system according to claim 1, wherein the at least one processing device is arranged to continuously determine and update the activity state for the monitored individual.

5. The system according to claim 1, wherein the predetermined state condition comprises the following:
an OUT OF BED alert state can only be set if the previous activity state was some type of LYING IN BED activity state, and
a FALL alert state can only be set if the previous activity state was not any type of LYING activity state.

6. The system according to claim 4, wherein the at least one processing device is arranged to set the alert based also on the time period for which the individual has had a specific activity state.

7. The system according to claim 4, wherein the determination the activity state is done by a trained machine learning algorithm.

8. The system according to claim 1, wherein the at least one processing device is further arranged to send an alarm signal if a predetermined alert is set.

9. The system according to claim 1, wherein the at least one motion sensor is an accelerometer.

10. The system according to claim 1, wherein the personal module is a wristworn device.

11. The system according to claim 1, wherein the personal module further comprises a personal module communication interface, and the at least one node module further comprises a node module communication interface, which are arranged to communicate with each other.

12. A method for monitoring an individual within predetermined facilities in order to determine whether there is a need for setting an alert, the method comprising:
receiving sensor data from at least one motion sensor arranged in a personal module;
determining whether the received sensor data indicates a specific alert state among a plurality of predetermined alert states, the alert states comprising at least a FALL alert state, to be used if a probable fall has been detected for the monitored individual, and an OUT OF BED alert state, to be used if it has been detected that the monitored individual is probably getting out of bed;
determining the distance between the personal module and at least one node module;
determining the location of the personal module within the facilities based at least on the determined distance together with information retrieved from a storage means regarding the layout of the facilities within which the monitoring of the individual takes place;

determining and updating an activity state for the monitored individual; and setting an alert based at least on: whether the received sensor data indicates an alert state; whether the determined location fulfils a predetermined location condition, indicating whether the individual is located in a certain room; and whether at least one previously determined activity state for the monitored individual fulfils a predetermined state condition.

13. The method according to claim 12, wherein the determining of whether the received sensor data indicates a specific alert state among a plurality of predetermined alert states is done by a trained machine learning algorithm.

14. The method according to claim 12, wherein the determining of the location of the personal module is based also on an indication of the movement of the individual in relation to a previously determined location, based on sensor data from the at least one motion sensor.

15. The method according to claim 12, comprising continuously determining and updating the activity state for the monitored individual.

16. The method according to claim 12, wherein the predetermined state condition comprises the following:

an OUT OF BED alert state can only be set if the previous activity state was some type of LYING IN BED activity state, and a FALL alert state can only be set if the previous activity state was not any type of LYING activity state.

17. The method according to claim 15, wherein the setting of the alert is based also on the time period for which the individual has had a specific activity state.

18. The method according to claim 15, wherein determining of the activity state is done by a trained machine learning algorithm.

19. The method according to claim 12, further comprising sending an alarm signal if a predetermined alert is set.

20. The method according to claim 12, wherein the personal module is a wristworn device.

\* \* \* \* \*